United States Patent
Bowe, Jr.

(10) Patent No.: US 6,763,704 B2
(45) Date of Patent: Jul. 20, 2004

(54) FOAM DETECTOR FOR CONCENTRATOR ATTACHMENT FOR GAS CHROMATOGRAPH

(75) Inventor: Woodford A. Bowe, Jr., Rising Sun, MD (US)

(73) Assignee: CDS Analytical, Inc., Oxford, PA (US)

( * ) Notice: Subject to any disclaimer, the term of this patent is extended or adjusted under 35 U.S.C. 154(b) by 59 days.

(21) Appl. No.: 10/220,685

(22) PCT Filed: Mar. 9, 2001

(86) PCT No.: PCT/US01/07698

§ 371 (c)(1),
(2), (4) Date: Sep. 3, 2002

(87) PCT Pub. No.: WO01/69264

PCT Pub. Date: Sep. 20, 2001

(65) Prior Publication Data

US 2003/0037600 A1 Feb. 27, 2003

Related U.S. Application Data

(60) Provisional application No. 60/188,639, filed on Mar. 10, 2000, and provisional application No. 60/224,242, filed on Aug. 10, 2000.

(51) Int. Cl.[7] .................. G01N 11/00; G01N 30/04
(52) U.S. Cl. ............ 73/53.01; 73/23.35; 73/23.4; 73/23.41; 73/64.55
(58) Field of Search .................. 73/23.22, 23.35, 73/23.4, 23.41, 53.01, 64.55

(56) References Cited

U.S. PATENT DOCUMENTS

| | | | | |
|---|---|---|---|---|
| 3,739,795 A | * | 6/1973 | Hyde et al. ............... 137/5 |
| 4,009,010 A | * | 2/1977 | Sauer et al. .............. 95/150 |
| 4,902,962 A | * | 2/1990 | Ishikawa ................ 324/690 |
| 4,987,082 A | * | 1/1991 | Gallagher ............... 435/246 |
| 4,997,660 A | * | 3/1991 | Wittler ................... 426/17 |
| 6,078,729 A | * | 6/2000 | Kopel .................... 392/402 |

* cited by examiner

Primary Examiner—Daniel S. Larkin
(74) Attorney, Agent, or Firm—Webb Ziesenheim Logsdon Orkin & Hanson, P.C.

(57) ABSTRACT

A foam detector generally including a pair of leads positioned adjacent to a surface layer of a fluid so that foam created on a surface layer of the fluid contacts at least one lead and sends a signal to a controller connected to the leads.

15 Claims, 5 Drawing Sheets

FOAM DETECTOR FOR CONCENTRATOR ATTACHMENT FOR GAS CHROMATOGRAPH

This application is a 35 U.S.C. 371 Application of PCT/US01/07698 filed Mar. 9, 2001, which is a divisional application of U.S. Provisional Patent Application No. 60/188,639, filed Mar. 10, 2000 and a divisional application of U.S. Provisional Patent Application No. 60/224,242, filed Aug. 10, 2000.

BACKGROUND OF THE INVENTION

1. Field of the Invention

The present invention relates to foam detectors and, more particularly, to foam detectors used in conjunction with a concentrator for gas chromatographs.

2. Brief Description of the Prior Art

When a gas is diffused through a fluid, bubbles can form and collect on a surface layer of the fluid. The accumulation of bubbles is commonly referred to as foam.

In some applications, such as in gas chromatography sample preparation, sample vessels are used to extract volatile organics from water samples or the like. A pressurized sparging gas is introduced into the water sample and diffuses through the water sample. The volatile organics are carried out of the water sample by the sparging gas and concentrated by a trap in a sample concentrator. The concentrated organics are then released from the trap and passed to an analyzing instrument, such as a gas chromatograph. If the bubbling action of the sparging gas creates foam over the surface layer of the water sample, the foam may or may not be contained or dissipated by a bubble breaker defined by the sample vessel. The presence of foam can lead to erroneous measurements or contamination of the sample concentrator. U.S. Pat. No. 4,910,996 to Pfisterer et al. discusses foaming problems in gas chromatographs used in beer processing. To combat the foam problem, the Pfisterer patent discloses using pressure regulators to pressurize a beer sample and prevent outgassing of the beer. However, if outgassing does occur, there is no way to test for the presence of the foam prior to the advancement of the concentrated prepared sample into internal tubing housed within the sample concentrator or the gas chromatograph.

Another problem not addressed by the prior art is the process of cleaning the sample concentrator if inadvertent contamination of the internal tubing does occur. Cleaning a contaminated sample concentrator generally takes a few weeks and includes the steps of taking the contaminated sample concentrator offline, shipping the sample concentrator to a cleaning facility, and reinstalling the cleaned sample concentrator.

SUMMARY OF THE INVENTION

To help obviate the disadvantages of the prior art, the present invention generally includes a device for detecting the presence of foam positioned adjacent to a surface layer of a fluid. The device generally includes a first lead positioned adjacent to the surface layer of the fluid, a second lead positioned adjacent to the surface layer of the fluid and spaced apart or electrically insulated from the first lead, and a controller connected to the first lead and the second lead. The first lead and the second lead may be thermocouples, with the first lead spaced at a further linear distance from the surface layer of the fluid than the second lead. Alternatively, the first lead and the second lead may be made from an electrically conductive material.

A method for the detection of foam positioned adjacent to a surface layer of a fluid is also provided. The method generally includes the steps of positioning a pair of leads adjacent to the surface layer of the fluid, with the leads each spaced apart or electrically insulated from one another. Additional steps include forming foam on the surface layer of the fluid, bringing the foam in physical contact with one or both of the pair of leads after the step of forming foam on the surface of the fluid, and registering a presence of the foam. Still further steps include (1) reducing the temperature of one of the leads after the step of bringing the foam in physical contact with one of the pair of leads and (2) flowing an electrical current from one of the pair of leads, through the foam, to another of the pair of leads, after the step of bringing the foam in physical contact with both of the pair of leads.

One particular application of the present invention is a system for detecting the presence of foam in gas chromatography. The system generally includes a gas chromatograph, a sample concentrator, such as a modular sample concentrator fluidly connected to the gas chromatograph, a sample vessel defining an internal cavity fluidly connected to the, sample concentrator, a pair of leads positioned in the internal cavity of the sample vessel, and a controller connected to the pair of leads. A fluid and foam may also be included, the fluid contained in the internal cavity of the sample vessel and the foam positioned on a surface layer of the fluid, wherein the foam physically touches at least one of the pair of leads. The modular sample concentrator may generally include a first body section housing, internal tubing, and a second body section housing control electronics, wherein the first body section and the second body section are removably connected to one another. Cleaning the sample concentrator includes the steps of removing a contaminated first body section from a second body section, replacing the contaminated first body section with a clean first body section, and resuming operation of the sample concentrator.

The present invention allows foam to be detected by one or both of the pair of leads, through the controller, and alert the operator so that the system can be shut down or continue to operate, depending on preprogram settings. Moreover, if the sample concentrator is contaminated by foam, the sample concentrator can be easily and quickly returned to operative service.

These and other advantages of the present invention will be clarified in the description of the preferred embodiments taken together with the attached drawings in which like reference numerals represent like elements throughout.

DETAILED DESCRIPTION OF THE PREFERRED EMBODIMENTS

The Applicants previously filed U.S. Provisional Patent Application Serial Nos. 60/188,639 and 60/224,242, which are both incorporated herein by reference in their entireties.

Figure 1:
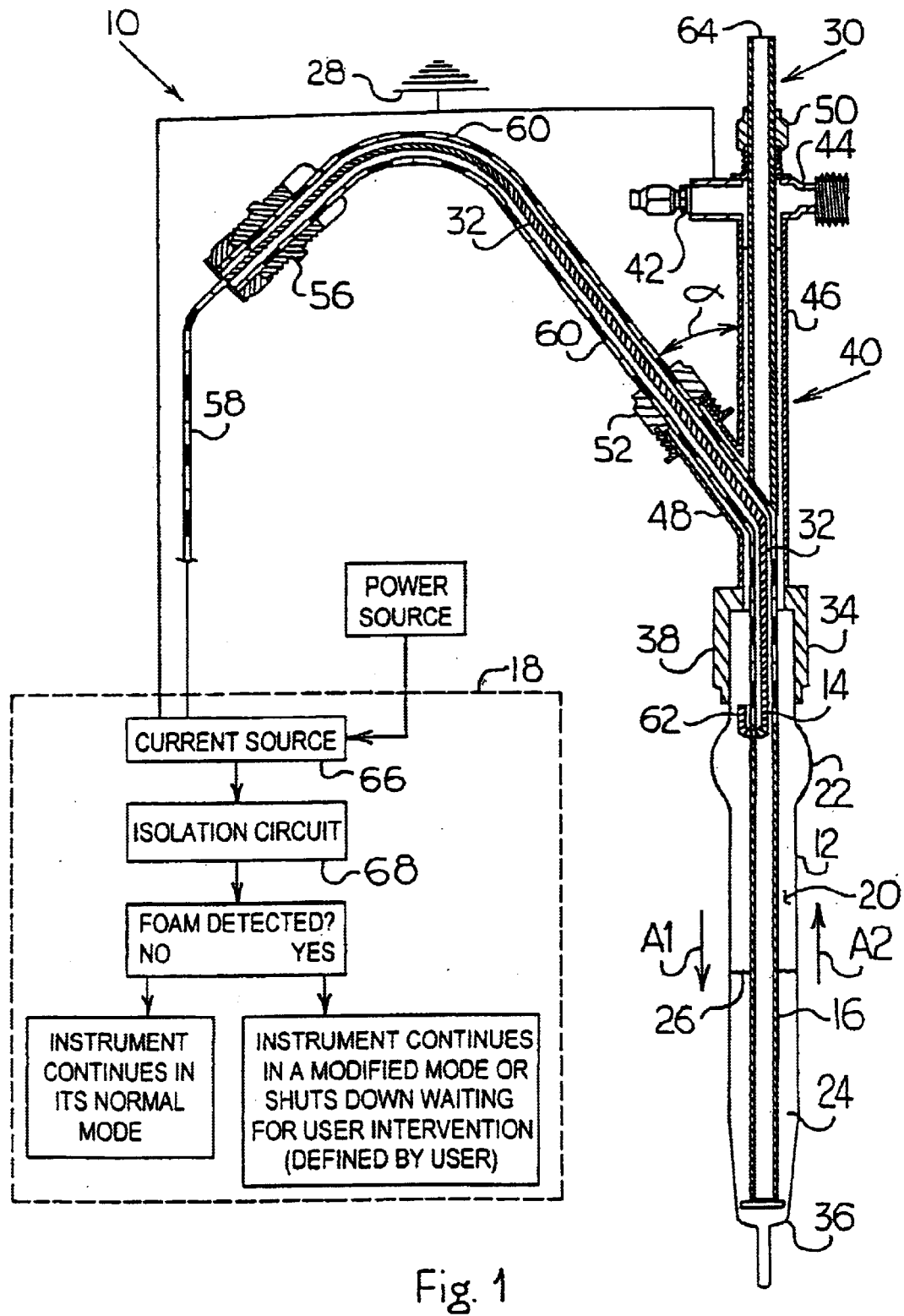
FIG. 1 is a sectional view of a first embodiment foam detector assembly according to the present invention.

A foam detector 10 according to a first embodiment of the present invention is shown in FIG. 1. The first embodiment foam detector 10 shown in FIG. 1 is shown in conjunction with a gas chromatography sample vessel 12 to help aid in the understanding of the present invention, but gas chromatography is only one possible type of application.

As shown in FIG. 1, the foam detector 10 generally includes a first lead 14, a second lead 16 electrically insulated from the first lead 14, and a controller 18 connected to the first lead 14 and the second lead 16. In the particular application shown in FIG. 1, the sample vessel 12 defines an internal cavity 20 and a bubble breaker 22, the internal cavity 20 receiving a fluid 24 having a surface layer 26. Moreover, the first lead 14 is a sensor wire 32 and the second lead 16 is a dip tube 30, which is electrically grounded 28.

The sample vessel 12 forms a first end 34 and a second end 36, and is generally made from glass or other electrically non-conductive material. A first collar 38 is preferably positioned adjacent to the first end 34 of the sample vessel 12 for receiving a housing 40. The housing 40 is generally a hollow structure defining an evacuation branch 42, a fill branch 44 with an optional septum retainer to allow for syringe injections, and a dip tube passageway 46, with the dip tube passageway 46 receiving the dip tube 30. An optional sensor conduit 48 is preferably fluidly connected to the dip tube passageway 46, and preferably extends away from the housing 40 at an angle α generally between 1 and 179 degrees. However, the sensor conduit 48 is not required if the housing 40 defines a sealed orifice or is otherwise configured to receive a sensor wire 32, discussed below. A second collar 50, configured to provide a fluid seal with the dip tube 30, is also positioned adjacent to the housing 40. As previously stated, the dip tube 30 preferably extends through the dip tube passageway 46 defined by the housing 40 and continues to extend in a direction away from the sample vessel 12 and the housing 40.

One end of the sensor wire 32 extends through the sensor conduit 48 connected to the housing 40 and is fluidly sealed to the housing 40 by a third collar 52. The other end of the sensor wire 32 is electrically connected to a vessel ferrule 56. The sensor wire 32 is preferably electrically conductive, such as a 0.010 inch diameter wire made from stainless steel or other suitable electrically conductive material. The vespel ferrule 56 is generally made from plastic and metal, metal, or any other suitable material or materials. A carrier wire 58, preferably made from 22-gauge copper or any other diameter of suitable material, is also connected to the vespel ferrule 56. An electrically insulated material 60, such as PEEK brand heat shrink tubing, preferably encompasses all of the electrically conductive parts. More specifically, the PEEK brand heat shrink tubing is sealingly captured in the vespel ferrule 56 and extends along with the sensor wire 32 through the sensor conduit 48, the dip tube passageway 46 in the housing 40, and into the internal cavity 20 defined by the sample vessel 12, terminating above the bubble breaker 22. The sensor wire 32 extends out of the electrically non-conductive material 60 and is bent back over the material 60. An exposed end 62 of the sensor wire 32 is arranged as not to contact the dip tube 30, which is preferably electrically grounded.

With continuing reference to FIG. 1, a sparging gas 64 flows through the dip tube 30 in the direction shown by arrow A1 and into the second end 36 of the sample vessel 12. The sparging gas 64 percolates through the fluid 24 introduced into the sample vessel 12, captures volatile organic analytes or other substances from the fluid 24, and carries the analytes out of the sample vessel 12 through the evacuation branch 42. If foam forms on the surface layer 26 of the fluid 24, the foam rises in a direction indicated by arrow A2 and enters the bubble breaker 22. When foam moves up beyond the bubble breaker 22 and contacts the exposed end 62 of the sensor wire 32 and the dip tube 30, current is drawn through the sensor wire 32 as the electrical discontinuity present between the spaced apart sensor wire 32 and dip tube 30 is closed by the foam. This current, produced by a current source 66 in the controller 18, is sensed by the controller 18 and a signal is generated indicative of foam beyond the bubble breaker 22. The signal passes though an isolation circuit 68 and foam detection logic is applied. The controller 18 is programmed to respond to the signal in a way specified by the user which may, for example, include shutting down the gas chromatography application to allow cleaning of sample vessel 12. The current source 66 is designed so that when foam contacts the sensor wire 32, current flows in a range of approximately 1–10 micro amps. The current is controlled by the voltages applied across the sensor wire 32 in the dip tube 30 and the additional series resistance. The current is so limited to minimize hydrolysis of the fluid 24 in the sample vessel 12.

Figure 2:
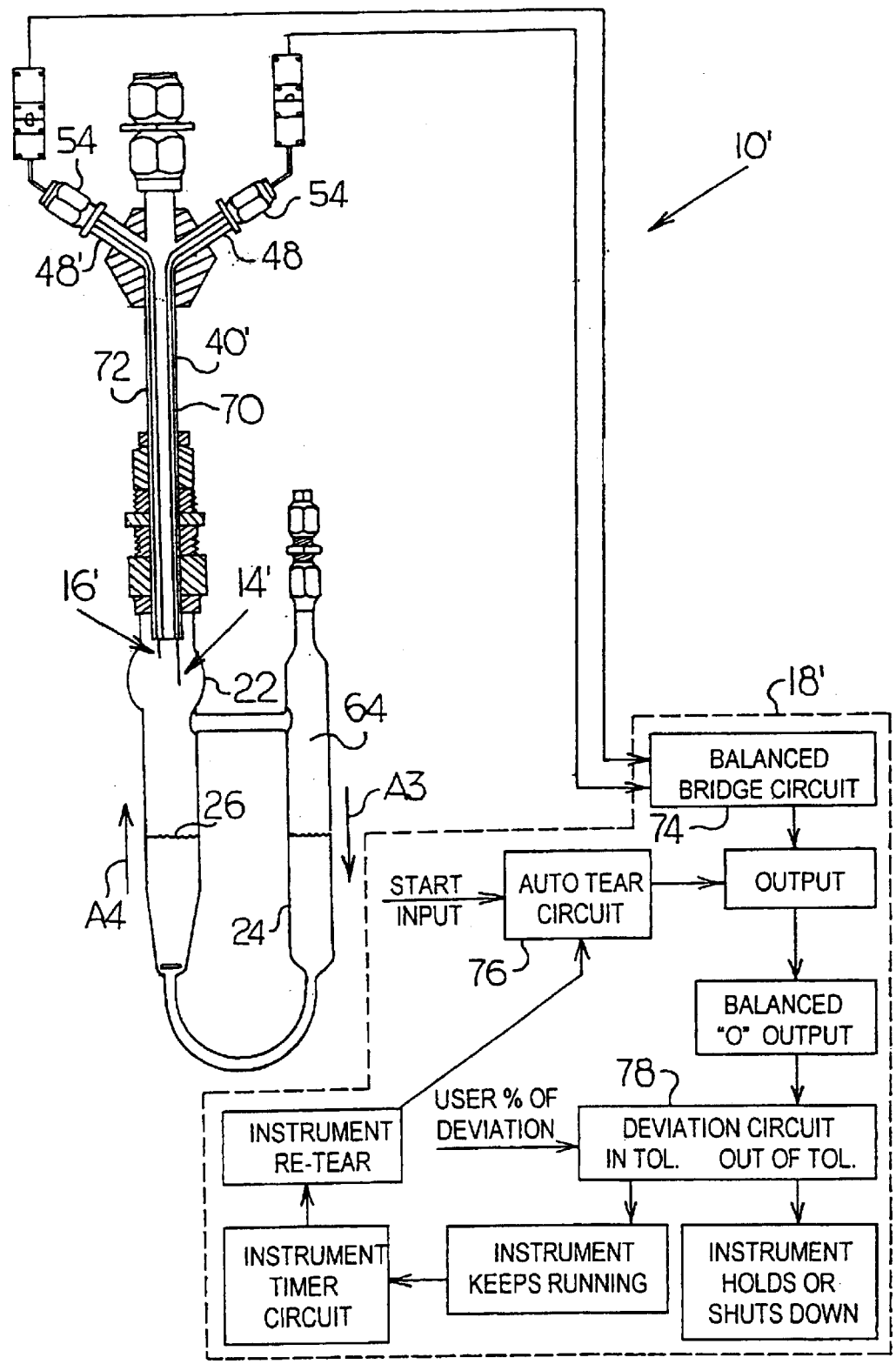
FIG. 2 is a sectional view of a second embodiment foam detector assembly according to the present invention.

A foam detector 10' according to a second embodiment of the present invention is shown in FIG. 2. The second embodiment foam detector 10' is also shown in connection with a gas chromatography application, but other applications are also contemplated. Moreover, when compared to FIG. 1, like parts in FIG. 2 are represented by like reference numerals.

In the second embodiment foam detector 10', as shown in FIG. 2, the housing 40' preferably has two sensor conduits 48, 48'. The first lead 14', such as a first thermocouple 70, is inserted through the sensor conduit 48, is sealed by fourth collar 54, and extends away from the housing 40' in a direction A3 toward the bubble breaker 22. The second lead 16', such as a second thermocouple 72, is inserted through the second sensor conduit 48', is sealed by a second fourth collar 54, and also extends away from the housing 40' in a direction toward the bubble breaker 22. The first lead 14' extends further away from the housing 40' than the second lead 16', so that the first lead 14' is spaced closer to the bubble breaker 22 than the second lead 16'.

With continuing reference to FIG. 2, sparging gas 64 flows through the sample vessel 12 in the direction of arrow A3 through the fluid 24. As the sparging gas 64 percolates through the fluid 24, volatile organic analytes or other substances are captured from the fluid 24 and exit the sample vessel 12 through a dip tube 30 (FIG. 1) which extends through the housing 40'. If foam forms on the surface layer 26 of the fluid 24, the foam rises in a direction indicated by arrow A4 and enters the bubble breaker 22. When foam moves up beyond the bubble breaker 22 and contacts the first lead 14', which is spaced closer to the bubble breaker 22 than the second lead 16', the foam cools the first lead 14', which, in this embodiment, is a first thermocouple 70. The cooling creates a temperature differential between the first thermocouple 70 and the second thermocouple 72. Any temperature difference between the first thermocouple 70 and the second thermocouple 72 results in a corresponding electrical differential. The electrical differential is measured by a controller 18' having a balanced bridge circuit 74 which is zeroed at startup using an autotear circuit 76. The balance bridge circuit 74 compares the electrical output of the first thermocouple 70 and the electrical output of the second thermocouple 72. The comparison of the first thermocouple 70 and the second thermocouple 72 can be adjusted using a user deviation circuit 78. The deviation circuit 78 can be used to correct for drift and other problems. Thermocouples 70, 72 are preferred in this embodiment because the thermocouples 70, 72 are in the same thermal environment in their respective electrical outputs are generally equal to one another. Therefore, if both the first and second thermocouples 70, 72 are heated or cooled equally, both will produce a zero output voltage or an output voltage normalized to zero.

If the difference between the electrical output of the first thermocouple 70 and the second thermocouple 72 exceeds the deviation entered by the user, the process or operation stops, holds, or shuts down, thereby preventing contamination and erroneous results. However, if the difference between the electrical output of the first thermocouple 70 and the second thermocouple 72 is within the tolerances set by the user, the process keeps running for the desired allotted period of time, stops, and the comparison zeroed itself. Only a sudden rise or fall in voltage outside the set tolerances causes shutdown. Continuous slow drift is neutralized by a periodic rezeroing of the output signals of the first and second thermocouples 70, 72.

Figure 3:
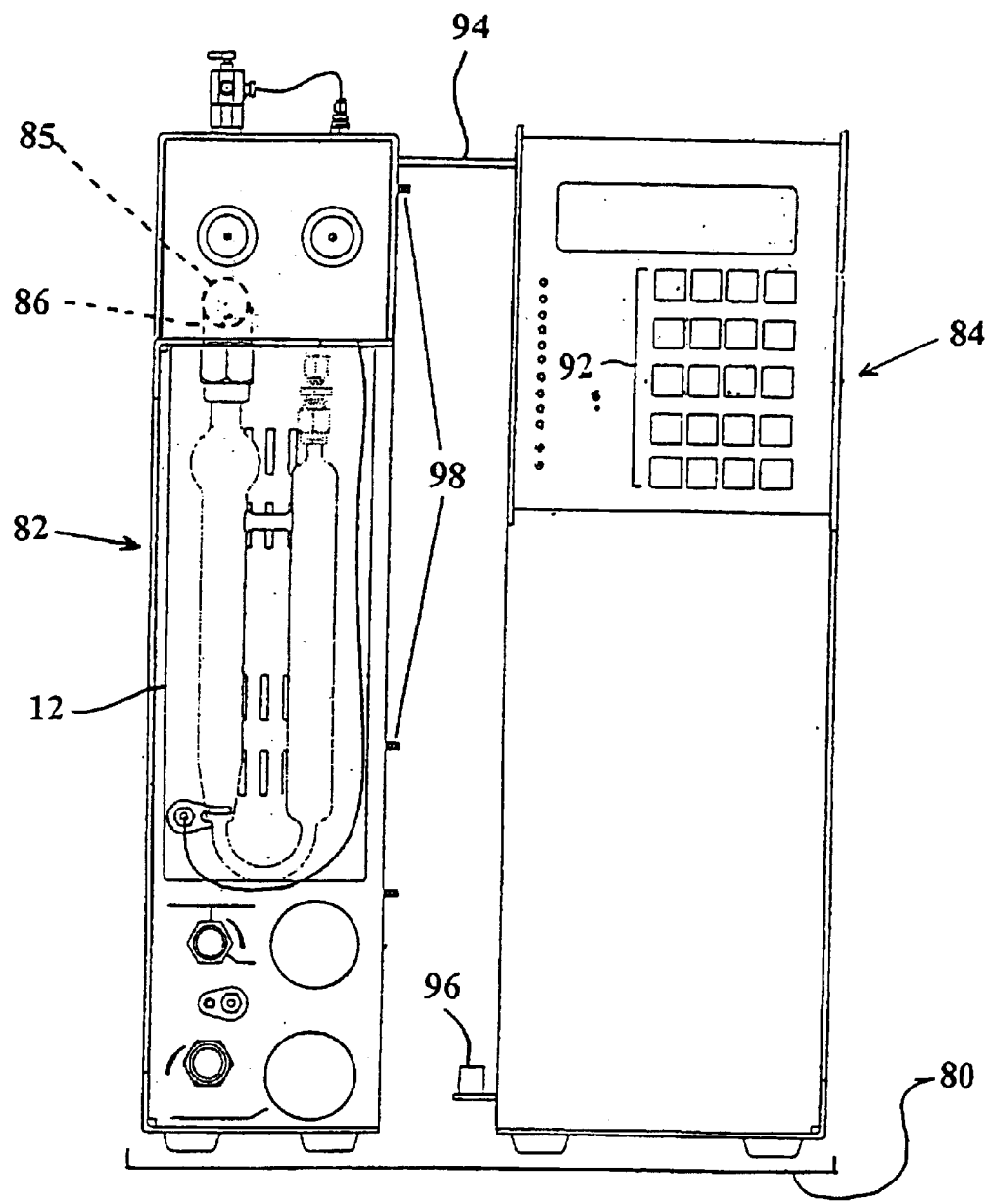
FIG. 3 is a first end view of a modular sample concentrator according to the present invention.
Figure 4:
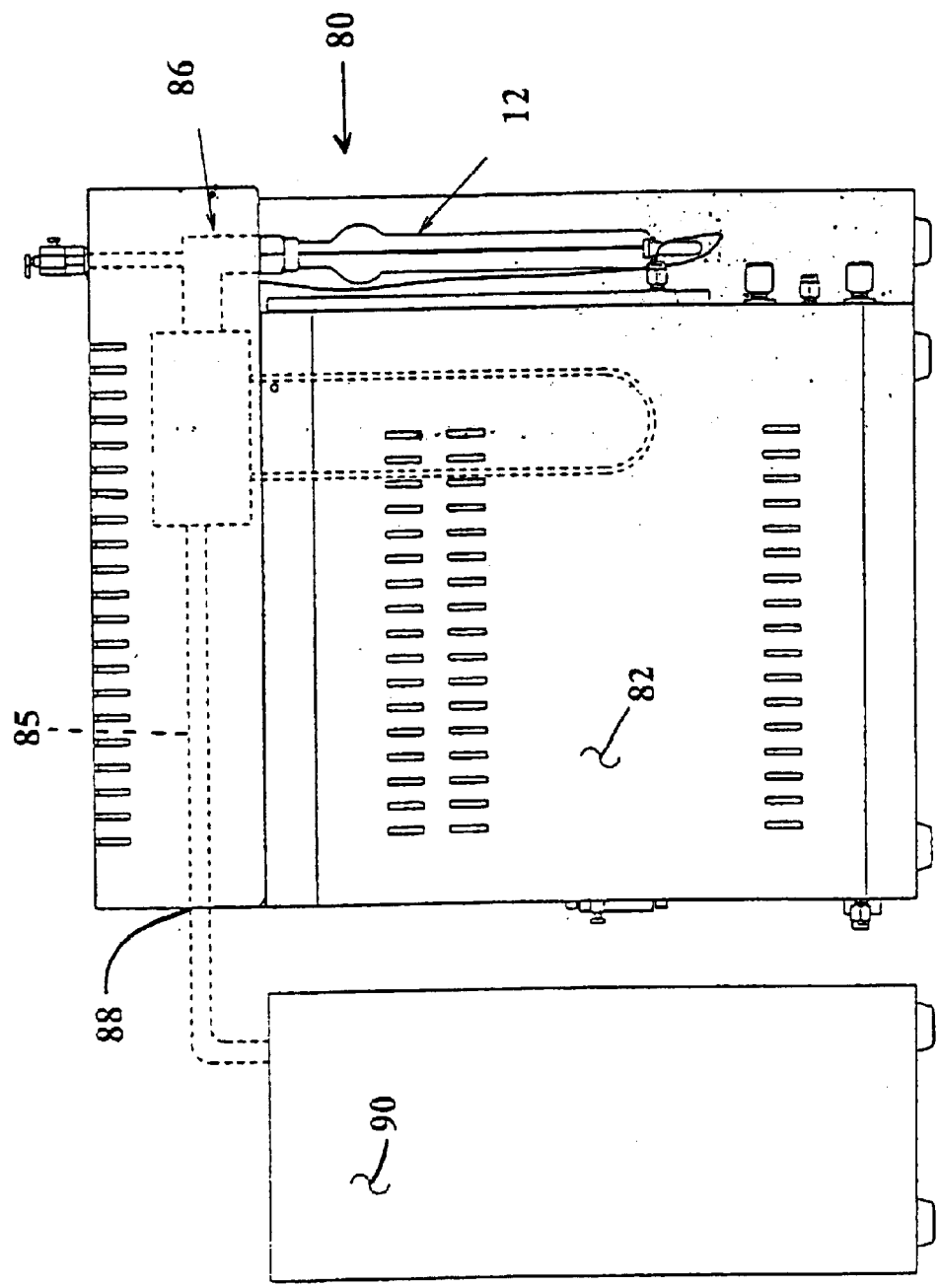
FIG. 4 is a side view of the modular sample concentrator shown in FIG. 3.
Figure 5:
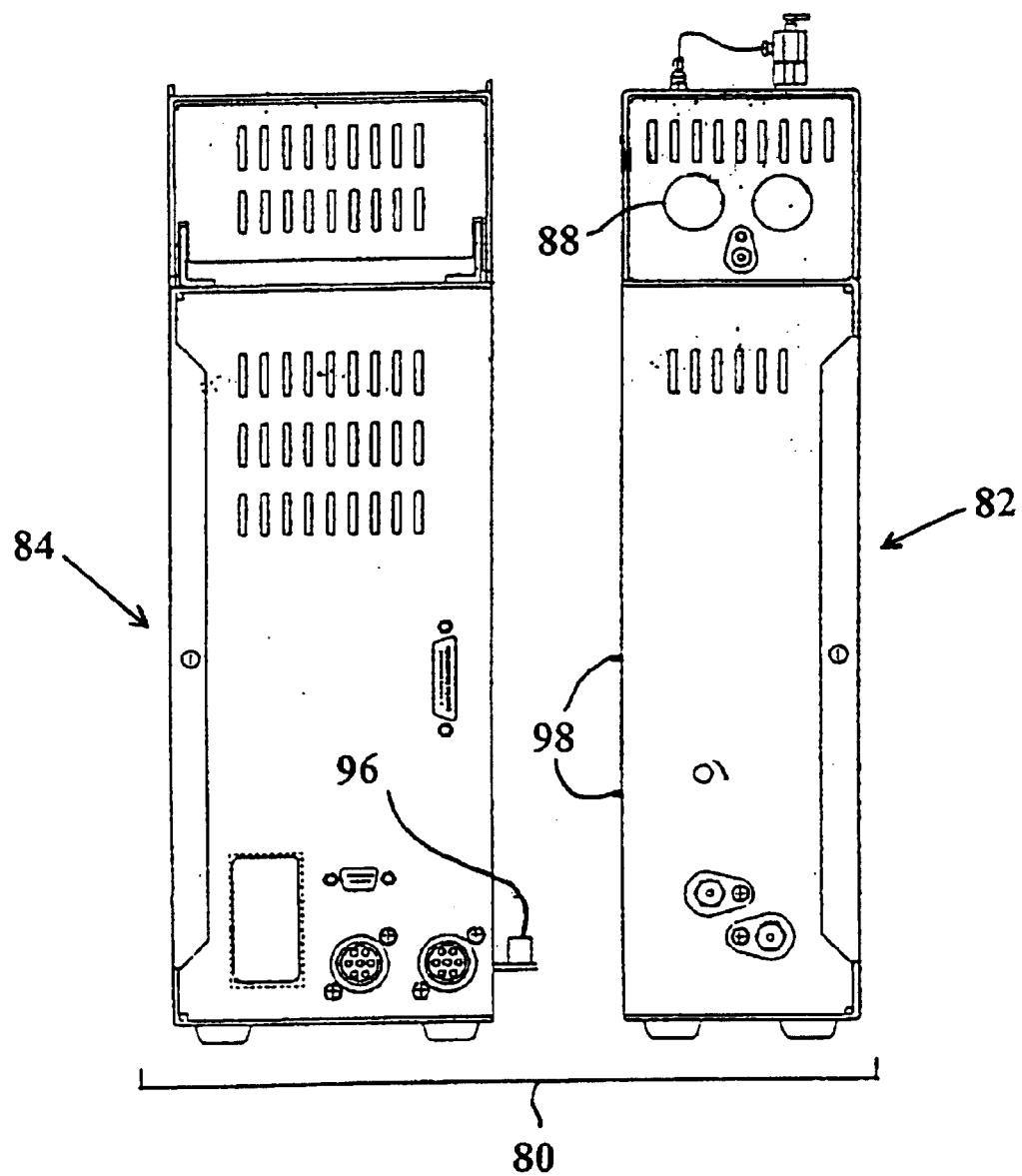
FIG. 5 is a second end view of the modular sample concentrator shown in FIGS. 3 and 4.

In the unlikely event that the first and second embodiment foam detectors 10, 10' become incapacitated due to wear, a modular sample concentrator 80, shown in FIGS. 3–5, can be used either in conjunction with the first and second embodiment foam detectors 10, 10' or without the first and second embodiment foam detectors 10, 10'. As shown in FIG. 3, the modular sample concentrator 80 generally includes a first body section 82 removably connected to a second body section 84. As shown generally in FIGS. 3 and 5, and with more detail in FIG. 4, the first body section 82 preferably houses internal tubing 85 which is fluidly connected at one end 86 to a sample vessel 12 and is fluidly connected at a second end 88 to a gas chromatograph 90. Referring again to FIG. 3, the second body section 84 houses electronic control circuitry and may also contain an input control panel 92. The first and second body sections 82, 84 are preferably electrically connected to each other via a wiring harness 94, an integrated circuit board 96, and one or more spring loaded attachment posts 98.

Referring generally to FIGS. 3–5, one method of repairing the modular sample concentrator 80 includes the steps of operating the modular sample concentrator 80, allowing the first body section 82 internal tubing 85 to become contaminated, stopping the modular sample concentrator 80, removing the first body section 82, replacing the removed first body section 82 with another first body section 82 having clean internal tubing 85, restarting the modular sample concentrator 80, and cleaning the contaminated first body section 82. This method allows the modular sample concentrator 80 to become operational quickly, without taking the entire modular sample concentrator 80 offline for one or more days.

The invention has been described with reference to the preferred embodiments. Obvious modifications and alterations will occur to others upon reading and understanding the preceding detailed description. It is intended that the invention be construed as including all such modifications and alterations insofar as they come within the scope of the appended claims or the equivalents thereof.

I claim:

1. A system for detecting the presence of foam positioned adjacent to a surface of a fluid in a sample vessel for a gas chromatograph, the system comprising:

a sample vessel;

a first electrically conductive lead positioned in the sample vessel adjacent to the surface layer of the fluid;

an electrically conductive dip tube positioned in the sample vessel and spaced away from the first electrically conductive lead; and a controller electrically connected to the first electrically conductive lead and the electrically conductive dip tube.

2. The system as claimed in claim 1 wherein the electrically conductive dip tube is spaced at a first linear distance from the foam than the first electrically conductive lead.

3. The system as claimed in the claim 1 wherein the first electrically conductive lead is electrically charged.

4. A method for the detection of foam positioned adjacent to a surface of a fluid comprising the steps of:

providing a sample vessel connected to a gas chromatograph;

positioning a pair of conductive leads inside the sample vessel, adjacent to the surface of the fluid;

forming foam on the surface of the fluid;

bringing the foam in physical contact with one of the pair of conductive leads;

changing a thermal temperature of the one of the pair of conductive leads with the foam; and registering a presence of the foam.

5. The method as claimed in claim 4 further comprising the step of spacing the pair of conductive leads away from one another after the step of positioning a pair of conductive leads inside the sample vessel, adjacent to the surface of the fluid.

6. The method as claimed in claim 4 wherein the pair of conductive leads is comprised of thermocouples.

7. A gas chromatography system comprising:

a gas chromatograph;

a modular sample concentration fluidly connected to the gas chromatograph, the modular sample concentrator comprising a first body section and a second body section, the first body section having internal tubing housed therein, the second body section having electronic control circuitry housed therein, and the first body section and the second body section removeably connected to each other;

a sample vessel defining an internal cavity, the internal cavity fluidly connected to the internal tubing housed in the first body section of the modular sample concentrator;

a pair of conductive leads positioned in the internal cavity of the sample vessel; and a controller connected to the pair of conductive leads.

8. The system as claimed in claim 7 wherein one of the pair of conductive leads is made from an electrically conductive material.

9. The system as claimed in claim 8 wherein the controller is a current source and an isolation circuit.

10. The system as claimed in claim 7 wherein one of the pair of conductive leads is an electrically conductive dip tube.

11. The system as claimed in claim 10 wherein the electrically conductive dip tube is electrically grounded and extends into the fluid and the foam.

12. The system as claimed in claim 7 wherein one of the pair of conductive leads is a thermo-conductive thermocouple.

13. The system as claimed in claim 12 wherein the controller is a balanced bridge circuit.

14. The system as claimed in claim 13 wherein the controller further comprises an auto tear circuit and a deviation circuit.

15. The system as claimed in claim 7 further comprising a fluid and foam, the fluid contained in the internal cavity of the sample vessel and the foam positioned on a surface of the fluid, wherein the foam physically touches at least one of the pair of conductive leads.

* * * * *